US007998926B2

(12) United States Patent
Marchalonis et al.

(10) Patent No.: US 7,998,926 B2
(45) Date of Patent: Aug. 16, 2011

(54) DIMERIZED T-CELL RECEPTOR FRAGMENT, ITS COMPOSITIONS AND USE

(75) Inventors: John Jacob Marchalonis, Tucson, AZ (US); Ronald Ross Watson, Tucson, AZ (US)

(73) Assignee: The Arizona Boad of Regents on Behfl of the University of Arizona, Tucson, AZ (US)

( * ) Notice: Subject to any disclaimer, the term of this patent is extended or adjusted under 35 U.S.C. 154(b) by 1771 days.

(21) Appl. No.: 10/478,194

(22) PCT Filed: May 17, 2002

(86) PCT No.: PCT/GB02/02323
§ 371 (c)(1),
(2), (4) Date: Jul. 28, 2004

(87) PCT Pub. No.: WO02/094860
PCT Pub. Date: Nov. 28, 2002

(65) Prior Publication Data
US 2004/0248192 A1 Dec. 9, 2004

(30) Foreign Application Priority Data
May 18, 2001 (GB) .................................. 0112126.8

(51) Int. Cl.
*A61K 38/10* (2006.01)
(52) U.S. Cl. ......................................... 514/3.8; 530/327
(58) Field of Classification Search .................. None
See application file for complete search history.

(56) References Cited

U.S. PATENT DOCUMENTS

| | | | |
|---|---|---|---|
| 5,714,577 A * | 2/1998 | Montelaro et al. ............ | 530/324 |
| 5,911,990 A | 6/1999 | Marchalonis et al. | |
| 5,962,319 A | 10/1999 | Ogawa et al. | |
| 6,150,337 A | 11/2000 | Tam | |
| 7,323,174 B1 * | 1/2008 | Marchalonis et al. ..... | 424/185.1 |
| 2002/0028211 A1 * | 3/2002 | Kaempfer et al. ......... | 424/190.1 |

FOREIGN PATENT DOCUMENTS

| | | |
|---|---|---|
| EP | 0 109 942 | 5/1984 |
| EP | 0 180 564 | 5/1986 |
| EP | 0 231 039 | 8/1987 |
| GB | 2 189 141 | 10/1987 |
| WO | WO 91/10736 | 7/1991 |
| WO | WO 92/01715 | 2/1992 |
| WO | WO 94/18317 | 8/1994 |
| WO | WO 95/18145 | 7/1995 |
| WO | WO 96/21028 | 7/1996 |
| WO | WO 97/35991 | 10/1997 |

OTHER PUBLICATIONS

Liang et al., Cell Immunol. Aug. 25, 1996;172(1):126-34.*
Colman et al., Research in Immunology, 1994; 145(1): 33-36.*
Lederman et al., Molecular Immunology 28: 1171-1181, 1991.*
Abaza et al. J Protein Chem. Oct. 1992;11(5):445-54.*
Janeway et al., Immunobiology, 5th Ed., Garland Science, p. 98 (2001).*
The Merck manual of diagnosis and therapy (Mark Beers and Robert Berkow, eds., Published by Merck Research Laboratories, 17th ed., 1999, pp. 2352-2355.*
Strom et al., Therapeutic Immunology edited by Austen et al., Blackwell Science, Cambridge, MA, 1996, pp. 451-456.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Allowed Claims for U.S. Appl. No. 09/591,789, filed Jun. 12, 2000 by Marchalonis et al, 2 pages.
Davis, M.M. et al. (1999). "T-Cell Antigen Receptors," Chapter 10 in *Fundamental Immunology*, Fourth Edition, Paul W.E. ed., Lippincott-Raven Publishers: Philadelphia, pp. 341-347.
Evavold, B.D. et al. (Dec. 1993). "Ticking the TCR: Selective T-Cell Functions Stimulated by Altered Peptide Ligands," *Immunology Today* 14(12):602-609. (abstract).
Gait, M.J. et al. (Oct. 1995). "Progress in Anti-HIV Structure-Based Drug Design," *Tibitech* 13:430-438.
Madrenas, J. et al. (Apr. 1996). "Variant TCR Ligands: New Insights into the Molecular Basis of Antigen-Dependent Signal Transduction and T-Cell Activation," *Seminars in Immunology* 8(2):83-101. (abstract).
Maggi, E. et al. (Jul. 8, 1994). "Ability of HIV to Promote a $T_H1$ to $T_H0$ Shift and to Replicate Preferentially in $T_H2$ and $T_H0$ Cells," *Science* 265:244-248.
Marchalonis, J.J. et al. (1994). "Synthetic Autoantigens of Immunoglobulins and T-Cell Receptors: Their Recognition in Aging, Infection, and Autoimmunity," *Society for Experimental Biology and Medicine*, pp. 129-147.
Marchalonis, J.J. et al. (2001). "T-Cell Receptor-Derived Peptides in Immunoregulation and Therapy of Retrovirally Induced Immunosuppression," *Critical reviews in Immunology* 21:57-74.
Öberg, B. et al. (Jul. 1990). "Screening for New Agents," *Eur. J. Clin. Microbiol. Infect Dis.* 9(7):466-471.
Romagnani, S. et al. (1994). "Tenth Anniversary Perspectives on AIDS : An Alternative View of the Th1/Th2 Switch Hypothesis in HIV Infection," *Aids Research and Human Retroviruses* 10(5): iii-ix.

(Continued)

Primary Examiner — Zachary Skelding
(74) Attorney, Agent, or Firm — Morrison & Foerster LLP

(57) ABSTRACT

Dimers of a peptide from the T-cell receptor (Cys Lys Pro Ile Ser Gly His Asn Ser Leu Phe Trp Tyr Arg Gln Thr) (SEQ ID NO:1) are disclosed for preventing the progression to AIDS in an animal model. Methods for delaying the progression to AIDS and restoring normal immunological responses in an animal model following infection are shown and comprise administering through various systemic routes dimeric T-cell receptor peptide Vβ CDR1 to restore normal levels of Th1 cytokines interleukin 2 and interferon-γ, which are suppressed following infection, and those of Th2 derived cytokines interleukin 5, interleukin 6, interleukin 10, and immunoglobulin G, which are stimulated following infection.

13 Claims, 7 Drawing Sheets

OTHER PUBLICATIONS

Figure 1:
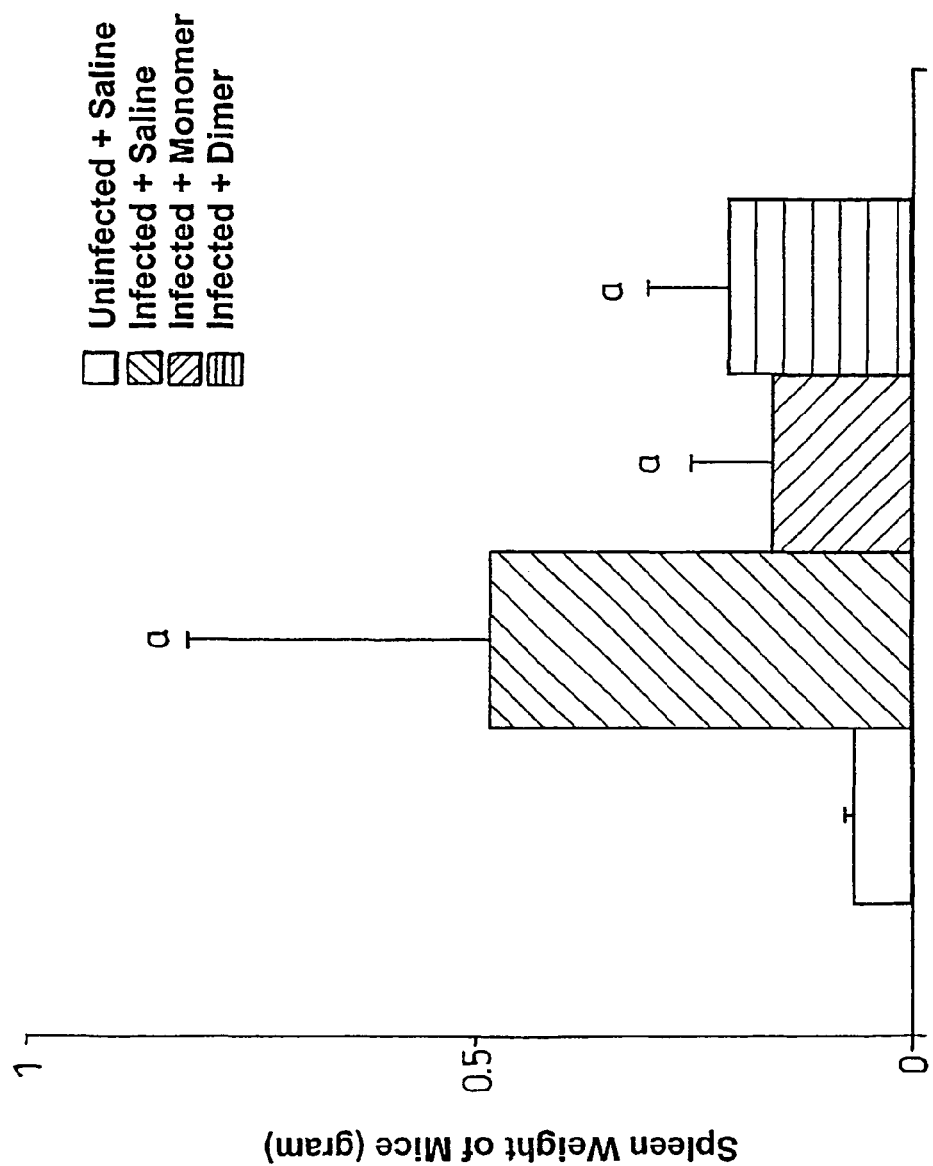

Sepulveda, R.T. et al. (Mar. 2003). "T-Cell Receptor Vβ8.1 Peptide reduces Cozsackievirus-Induced Cardiopathology During Murine Acquired Immunodeficiency Syndrome," *Cardiovasc Pharmacol* 41(3):489-497.

Shearer, G.M. et al. (1992). "T Helper Cell Immune Dysfunction in Asymptomatic HIV-1-Seropositive Individuals: The Role of TH1-TH2 Cross-Regulation," *Chem Immunol* 54:21-43.

U.S. Appl. No. 09/591,789, filed Jun. 12, 2000, by Marchalonis et al, 41 pages.

Yarchoan, R. et al. (1992). "Correlations Between the in Vitro and in Vivo Activity of Anti-HIV Agents: Implications for Future Drug Development," *J. Enzyme Inhibition* 6:99-111.

Akuffo, H. et al. (1999). "Natural Killer Cells in Cross-Regulation of IL-12 by IL-10 *Leishmania* Antigen-Stimulated Blood Donor Cells," *Clin. Exp. Immunol.* 117:529-534.

Albright, J.W. et al. (2000). "Soluble Receptors and Other Substances That Regulate Proinflammatory Cytokines in Young and Aging Humans," *J. Gerontol.* 55A(1):B20-B25.

Aleman, M. et al. (2000). "Interleukin-12 Amplifies the *M. leprae* hsp65-Cytotoxic Response in the Presence of Tumour Necrosis Factor-α and Interferon-γ Generating CD56+ Effector Cells: Interleukin-4 Downregulates This Effect," *Scand. Immunol.* 51:262-270.

Boon, T. (1993). "Tumor Antigens Recognized by Cytolytic T Lymphocytes: Present Perspectives for Specific Immunotherapy," *Int. J. Cancer* 54:177-180.

Bourdette, D.N. et al. (1994). "Immunity to TCR Peptides in Multiple Sclerosis. 1. Successful Immunization of Patients with Synthetic Vβ 5.2 and Vβ6.1 CDR2 Peptides," *J. Immunol.* 152:2510-2519.

Bradley, W.G. et al. (1994). "Alteration of in Vivo Cytokine Gene Expression in Mice Infected with a Molecular Clone of the Defective MAIDS Virus," *J. AIDS* 7:1-9.

Castle, S. et al. (1997). "Evidence of Enhanced Type 2 Immune Response and Impaired Upregulation of a Type 1 Response in Frail Elderly Nursing Home Residents," *Mech. of Ageing & Devel.* 94:7-16.

Cherwinski, H.M. et al. (1987). "Two Types of Mouse Helper T Cell Clone. III. Further Differences in Lymphokine Synthesis Between Th1 and Th2 Clones Revealed by RNA Hybridization, Functionally Monospecific Bioassays, and Monoclonal Antibodies," *J. Exp. Med.* 166:1229-1244.

Clerici, M. et al. (1993). "A $T_H1 \rightarrow T_H2$ Switch is a Critical Step in the Etiology of HIV Infection," *Immunol. Today* 14(3):107-110.

De Carli, M. et al. (1994). "Human Th1 and Th2 Cells Functional Properties, Regulation of Development and Role in Autoimmunity," *Autoimmunity* 18:301-308.

Dehghanpisheh, K. et al. (1995). "Production of IgG Autoantibodies to TCRs in Mice Infected with the Retrovirus LP-BM5," *Intl. Immunol.* 7(1):31-36.

Dehghanpisheh, K. et al. (1997). "Retrovirally Induced Mouse Anti-TCR Monoclonals Can Synergize the In Vitro Proliferative T Cell Response to Bacterial Superantigens," *Scand. J. Immunol.* 45:645-654.

Fauci, A.S. (1993). "Multifactorial Nature of Human Immunodeficiency Virus Disease: Implications for Therapy," *Science* 262:1011-1018.

Fernández-Gutiérrez, B. et al. (1999). "Early Lymphocyte Activation in Elderly Humans: Impaired T and T-Dependent B Cell Responses," *Exp. Gerontol.* 34:217-229.

Garcia, V.E. et al. (1999). "IL-18 Promotes Type 1 Cytokine Production From NK Cells and T Cells in Human Intracellular Infection," *J. Immunol.* 162:6114-6121.

Gazzinelli, R.T. et al. (1992). "Preferential Activation of Th2 Cells During Progression of Retrovirus-Induced Immunodeficiency in Mice," *J. Immunol.* 148(1):182-188.

Graziosi, C. et al. (1994). "Lack of Evidence for the Dichotomy of $T_H1$ and $T_H2$ Predominance in HIV-Infected Individuals," *Science* 265:248-252.

Graziosi, C. et al. (1996). "Kinetics of Cytokine Expression During Primary Human Immunodeficiency Virus Type 1 Infection," *Proc. Natl. Acad. Sci. USA* 93:4386-4391.

Haynes, B.F. et al. (1996). "Toward an Understanding of the Correlates of Protective Immunity to HIV Infection," *Science* 271:324-328.

Hirsch, C.S. et al. (1999). "Depressed T-Cell Interferon γ Responses in Pulmonary Tuberculosis: Analysis of Underlying Mechanisms and Modulation With Therapy," *J. Infect. Dis.* 180:2069-2073.

Imberti, L. et al. (1991). "Selective Depletion in HIV Infection of T Cells That Bear Specific T Cell Receptor $V_\beta$ Sequences," *Science* 254:860-862.

Infante-Duarte, C. et al. (1999). "Th1/Th2 Balance in Infection," *Springer Semin Immunopathol.* 21:317-338.

Ishikawa, T. et al. (1998). "Polyclonality and Multispecificity of the CTL Response to a Single Viral Epitope," *J. Immunol.* 161:5842-5850.

Jolly, C.A. et al. (1999). "Calorie Restriction Modulates Th-1 and Th-2 Cytokine-Induced Immunoglobulin Secretion in Young and Old C57BL/6 Cultured Submandibular Glands," *Aging Clin. Exp. Res.* 11:383-389.

Kanagawa, O. et al. (1993). "Resistance of Mice Deficient in IL-4 to Retrovirus-Induced Immunodeficiency Syndrome (MAIDS)," *Science* 262:240-242.

Karanfilov, C.I. et al. (1999). "Age-Related Defects in Th1 and Th2 Cytokine Production by Human T Cells Can Be Dissociated From Altered Frequencies of CD45RA+ and CD45RO+ T Cell Subsets," *Mech. Ageing Dev.* 109:97-112.

Kawakami, Y. et al. (1997). "Human Tumor Antigens Recognized by T-Cells," *Immunol. Res.* 16:313-339.

Kenney, R.T. et al. (1999). "Protective Immunity Using Recombinant Human IL-12 and Alum as Adjuvants in a Primate Model of Cutaneous Leishmaniasis," *J. Immunol.* 163:4481-4488.

Kimura, M. et al. (2000). "IL-4 Production by PBMCs on Stimulation with Mite Allergen is Correlated With the Level of Serum IgE Antibody Against Mite in Children with Bronchial Asthma," *J. Allergy Clin. Immunol.* 105:327-332.

Klein, S.A. et al (1997). "Demonstration of the Th1 to Th2 Cytokine Shift During the Course of HIV-1 Infection Using Cytoplasmic Cytokine Detection on Single Cell Level by Flow Cytometry," *AIDS* 11:1111-1118.

Lake, D.F. et al. (1994). "Autoantibodies to the α/β T-cell Receptors in Human Immunodeficiency Virus Infection: Dysregulation and Mimicry," *Proc. Natl. Acad. Sci. USA* 91:10849-10853.

Leigh, J.E. et al. (1998). "Th1/Th2 Cytokine Expression in Saliva of HIV-Positive and HIV-Negative Individuals: A Pilot Study in HIV-Positive Individuals with Oropharyngeal Candidiasis," *J. Acquir. Immune Defic. Syndr. Hum. Retrovirol.* 19:373-380.

Liang, B. et al. (1996). "Effects of Vaccination Against Different T Cell Receptors on Maintenance of Immune Function During Murine Retrovirus Infection," *Cell. Immunol.* 172:126-134.

Liang, B. et al. (1996). "Murine AIDS, a Key to Understanding Retrovirus-Induced Immunodeficiency," *Viral Immunol.* 9(4):225-239.

Liang, B. et al. (1996). "T-Cell-Receptor Dose and the Time of Treatment During Murine Retrovirus Infection for Maintenance of Immune Function," *Immunology* 87:198-204.

Liang, B. et al. (1997). "Prevention of Immune Dysfunction, Vitamin E Deficiency and Loss of *Crytosporidium* Resistance During Murine Retrovirus Infection by T Cell Receptor Peptide Immunization," *Nutr. Res.* 17(4):677-692.

Liang, B. et al. (1997). "Prevention of Retrovirus-Induced Aberrant Cytokine Secretion, Excessive: Lipid Peroxidation and Tissue Vitamin E Deficiency by T Cell Receptor Peptide Treatments in C57BL/6 Mice," *Proc. Soc. Exp. Biol. Med.* 214:87-94.

Liang, B. et al. (1998). "Injection of T-Cell Receptor Peptide Reduces Immunosenescence in Aged C57BL/6 Mice," *Immunology* 93:462-468.

Lohoff, M. et al. (1998). "Experimental Murine Leishmaniasis and the Th1/Th2 Cell Concept," *Tokai J. Exp. Clin. Med.* 23(6):347-350.

Longenecker, B.M. et al. (1993). "Immune Responses of Mice and Human Breast Cancer Patients Following Immunization with Synthetic Sialyl-Tn Conjugated to KLH Plus Detox Adjuvant," *Ann. NY Acad. Sci.* 690:276-291.

Marchalonis, J.J. et al .(1999). "Recognition of Defined Epitopes by Affinity-Purified Anti-Immunoglobulin Fab Autoantibodies Isolated From HIV-Infected Humans," *J. Mol. Recognition* 12:169-176.

Marchalonis, J.J. et al. (1992). "Human Autoantibodies Reactive with Synthetic Autoantigens From T-cell Receptor β Chain," *Proc. Natl. Acad. Sci: USA* 89:3325-3329.

Marchalonis, J.J. et al. (1993). "Natural Human Antibodies to Synthetic Peptide Autoantigens: Correlations with Age and Autoimmune Disease," *Gerontology* 39(2):65-79. Abstract Only.

Marchalonis, J.J. et al. (1994). "Autoantibodies to T-cell Receptors Following Infection by Murine Retrovirus," *Lymphology* 27S:853-856.

Marchalonis, J.J. et al. (1995). "Autoantibodies Against Peptide-Defined Epitopes of T-cell Receptors in Retrovirally Infected Humans and Mice," *Advances in Experimental Medicine and Biology* 383:211-222. Abstract Only.

Marchalonis, J.J. et al. (1997). "Analysis of Autoantibodies to T-Cell Receptors Among HIV-Infected Individuals: Epitope Analysis and Time Course," *Clin. Immunol. Immunopathol.* 82(2):174-189.

Marchalonis, J.J. et al. (1997). "Binding of Human IgG Myeloma Proteins to Autologous T-Cell Receptor Determinants," *Crit. Rev. Immunol.* 17:497-506.

Marchalonis, J.J. et al. (1997). "Use of Synthetic T-Cell Receptor Derived Peptides in Therapy for Autoimmunity and Retroviral Infections," *The Chemist* 74:3-9.

Marchalonis, J.J. et al. (2000). "Epitope Promiscuity of Human Monoclonal Autoantibodies to T-Cell Receptor Combining Site Determinants," *Appl. Biochem. Biotechnol.* 83(1-3):31-39.

Meroni, L. et al. (1996). "Evidence for Type 2 Cytokine Production and Lymphocyte Activation in the Early Phases of HIV-1 Infection," *AIDS* 10:23-30.

Mézière, C. et al. (1997). "In Vivo T Helper Cell Response to Retro-Inverso Peptidomimetics," *J. Immunol.* 159:3230-3237.

Mitra, D.K. et al. (1999). "Differential Representations of Memory T Cell Subsets are Characteristic of Polarized Immunity in Leprosy and Atopic Diseases," *Int. Immunol.* 11(11):1801-1810.

Moraes, M.O. et al. (1999). "Cytokine mRNA Expression in Leprosy: A Possible Role For Interferon-γ and Interleukin-12 in Reactions (RR and ENL)," *Scand. J. Immunol.* 50:541-549.

Moreland, L.W. et al. (1996). "Vβ17 T Cell Receptor Peptide Vaccination in Rheumatoid Arthritis: Results of Phase I Dose Escalation Study," *Journ. of Rheumatology* 23(8):1353-1362.

Moreland, L.W. et al. (1998). "T Cell Receptor Peptide Vaccination in Rheumatoid Arthritis: A Placebo-Controlled Trial Using a Combination of $V_\beta 3$: $V_\beta 14$, and $V_\beta 17$ Peptides," *Arth. Rheum.* 41(11):1919-1929.

Mosmann, T.R. et al. (1986). "Two Types of Murine Helper T Cell Clone. I. Definition According to Profiles of Lymphokine Activites and Secreted Proteins," *J. Immunol.* 136(7):2348-2357.

Mosmann, T.R. et al. (1991). "The Role of IL-10 in Crossregulation of Th1 and Th2 Responses," *Immunol. Today* 12:A49-A53.

Moudgil, K.D. et al. (1998). "Heterogeneity of the T Cell Response to Immunodominant Determinants Within Hen Eggwhite Lysozyme of Individual Syngeneic Hybrid $F_1$ Mice: Implications for Autoimmunity and Infection," *J. Immunol.* 161:6046-6053.

Movérare, R. et al. (2000). "Study of the Th1/Th2 Balance, Including IL-10 Production, in.Cultures of Peripheral Blood Mononuclear Cells from Birch-Pollen-Allergic Patients," *Allergy* 55:171-175.

Robey, I.F. et al. (2000). "Production and Characterization of Monoclonal IgM Autoantibodies Specific for the T-cell Receptor," *Journal of Protein Chemistry* 19(1):9-21. Abstract only.

Rocha, P.N. et al. (1999). "Down-Regulation of Th1 Type of Response in Early Human American Cutaneous Leishmaniasis," *J. Infect. Dis.* 180:1731-1734.

Romagnani, S. (1995). "Biology of Human $T_H1$ and $T_H2$ Cells," *J. Clin. Immunol.* 15(3):121-129.

Selvey, L.A. et al (1993). "Preferential Expansion and Activation of V β $5^+$ $CD4^+$ T Cells in Murine Acquired Immunodeficiency Syndrome," *J. Immunol.* 151(3):1712-1722.

Sher, A. et al. (1992). "Role of T-Cell Derived Cytokines in the Downregulation of Immune Responses in Parasitic and Retroviral Infection," *Immunol. Rev.* 127:183-204.

Solana, R. et al. (2000). "NK and NK/T Cells in Human Senescence," *Vaccine* 18:1613-1620.

Soudeyns, H.N. et al. (1993). "The T Cell Receptor Vβ Repertoire in HIV-1 Infection and Disease," *Semin. Immunol.* 5:175-185.

Timm, J.A. et al. (1999). "Maturation of CD4+ Lymphocytes in the Aged Microenvironment Results in a Memory-Enriched Population," *J. Immunol.* 162:711-717.

Valentin, A. et al. (1998). "Dual Effect of Interleukin 4 on HIV-1 Expression: Implications for Viral Phenotypic Switch and Disease Progression," *Proc. Natl. Acad. Sci. USA* 95:8886-8891.

Vandenbark, A.A. (1996). "Treatment of Multiple Sclerosis with T-Cell Receptor Peptides: Results of a Double-Blind Pilot Trial," *Nature Medicine* 2(10):1109-1115.

Victor-Korbin, C. et al. (1989). "Structural Correlates of a Regulatory Idiotype," *Immunol Rev.* 110:151-171.

Vigano, A. et al. (1995). "Immunologic Characterization of Children Vertically Infected with Human Immunodeficiency Virus, with Slow or Ripid Disease Progression," *J. Pediatri.* 126:368-374.

Wang, Y. et al. (1993). "The Kinetics of Imbalanced Cytokine Production by T Cells and Macrophages During the Murine AIDS," *Adv. Biosci.* 86:335-340.

Wang, Y. et al. (1994). "Anti-IL-4 Monoclonal Antibody, and IFN-γ Administration Retards Development of Immune Dysfunction and Cytokine Dysregulation During Murine AIDS," *Immunolgy* 83:384-389.

Watson, R.R. (1989). "Minireview: Murine Models for Acquired Immune Deficiency Syndrome," *Life Sciences* 44:iii-xv.

Watson, R.R. et al. (1995). "T Cell Receptor Vβ Complementarity-Determining Region 1 Peptide Administration Moderates Immune Dysfunction and Cytokine Dysregulation Induced by Murine Retrovirus Infection," *Journal of Immunolgy* 155(4):2282-2291.

Wilson, D.B. et al. (1997). "Results of a Phase I Clinical Trial of a T-Cell Receptor Peptide Vaccine in Patients with Multiple Sclerosis. I. Analysis of T-Cell Receptor Utilization in CSF Cell Populations," *J. Neuroimmunology* 76:15-28.

Yanagi, Y. et al. (1984). "A Human T Cell-Specific cDNA Clone Encodes a Protein Having Extensive Homology to Immunoglobulin Chains," *Nature* 308:145-149.

Yssel, H. et al (2000). "Characterization of T Cell Subpopulations Involved in The Pathogenesis of Asthma and Allergic Diseases," *Int. Arch. Allergy Immunol.* 121:10-18.

\* cited by examiner

DIMERIZED T-CELL RECEPTOR FRAGMENT, ITS COMPOSITIONS AND USE

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. HL59794 and HL63667 awarded by the National Institutes of Health.

The present invention relates generally to preparations for use in treating various disorders and diseases, including HIV and AIDS. Unlike most present efforts now being made to treat HIV and AIDS with antiviral drugs, and the push to develop new antiviral drugs that are effective for treating AIDS, the present invention relates to the use of a peptide derived from human T-cell receptors, and more specifically to dimers of the peptide.

Acquired immune deficiency syndrome (AIDS) is a disease of retroviral etiology, characterized by immune dysfunction, opportunistic infections, and eventually death. Murine acquired immune deficiency syndrome (MAIDS), induced by infection with the murine LP-BM5 leukemia retrovirus (MuLV) mixture, causes a progressive and profound immunodeficiency. It is strikingly similar to human AIDS, with splenomegaly, lymphadenopathy, and hypergammaglobulinemia in the early stage of retrovirus infection, progressive defects in T and B cell function, and reduction of host resistance to pathogens and neoplasia. These similarities exist even though human immunodeficiency virus (HIV), a lentivirus, and the retrovirus causing murine AIDS, MuLV, a C-type retrovirus, represent different types of retroviruses (1).

The immunopathogenic mechanisms underlying HIV infection and disease are not unidimensional; they are extremely complex (2). Preferential expansion, deletion, and activation of some CD4+ αβ T cells induced by retroviral super or chronic antigen (Ag) exposure in human and murine AIDS may be important immunopathogenic mechanisms (3-5). Selective Ag activation of CD4+ αβ T cells may lead to polyclonal stimulation of T and B cells at early stages, with subsequent aberrant cytokine production CD4+ T cell depletion. Eventually, these abnormalities lead to profound immunosuppression of cell-mediated immunity and immunodeficiency (2).

The aberrant cytokine production due to retrovirus infection, caused by a switch from T helper 1 (Th1) response to T helper 2 (Th2) response, promotes the progression to AIDS (6). In HIV+/AIDS patients and MuLV-infected mice, T cell proliferation and Th1 cytokine (interleukin-2 (IL-2) and interferon-γ) production decline, while Th2 cytokine (IL-4, IL-5, IL-6, and IL-10), and Ig production increase (7-10). The Th1 to Th2 conversion may determine the fatal outcome of the disease as part of the mechanism producing severe immunodeficiency and loss of disease resistance during the progression to AIDS.

When IL-4-deficient mice (IL-4 gene knockout) that are defective in Th2 cytokine responses are infected with LP-BM5 retrovirus, there is no lethality, and the development of T cell abnormalities associated with murine retrovirus infection is delayed (11). Administration of anti-IL-4 monoclonal antibody (mAb) to LP-BM5 retrovirus-infected mice or restoring the Th1 cytokine, IFN, by injection also normalizes the imbalance of Th1 and Th2 responses induced by retrovirus infection, prevents retrovirus-induced suppression of immune responses, and alleviates the typical murine AIDS symptoms: splenomegaly and hypergammaglobulinemia (12).

Autoantibodies (AAb) binding a peptide determinant corresponding to the first complementarity determining region (CDR1) of the T-cell receptor (TCR) Vβ domain were elevated early in murine retrovirus infection (13). Elevation of the levels of these AAbs is an early event following retroviral infection that corresponds in part to the general polyclonal activation of B cells with selectivity for particular Vβ sequences that occurs later. The production of high levels of anti-TCR AAb early in this disease with continued production of some AAbs suggests that they might be involved in retrovirus immunopathogenesis. The AAb directed against CDR1 determinants can be considered natural Ab against public or regulatory idiotypes (Id) (14), since this region is the least variable of the CDR and is completely specified by the Vβ gene sequence.

Preferential expansion of some TCR αβ CD4+ T cells induced by retroviral superantigens in both human and murine retrovirus infection is an important immunopathogenic mechanism (2, 5). Selective expansion/deletion of some TCR αβ CD4+ T cells may lead to polyclonal activation of T and B cells at an early stage, and subsequent aberrant cytokine production. Eventually these abnormalities lead to profound immunodeficiency with immunosuppression of cell-mediated immunity.

The present invention provides T-cell receptor (TCR) peptide preparations which, when administered to a host infected with an immunodeficiency-type retrovirus, are effective in preventing the progression to AIDS. The present invention also provides methods for preventing the progression to AIDS in an infected host, comprising administering the TCR Vβ CDR1 preparation to an infected host by various systemic routes, thus arresting the development of the immune dysfunction and cytokine dysregulation which allows retrovirus infections to weaken host defences to pathogens.

The use of TCR Vβ CDR1 peptides in the treatment of infected hosts to prevent progression to AIDS is disclosed in U.S. Pat. No. 5,911,990. Unexpectedly, we have found that dimerised TCR Vβ CDR1 peptides are as least as effective a treatment as TCR Vβ CDR1 monomers. In this regard, FIGS. 1 to 7 show that Vβ3 peptide dimers are at least as effective as the monomer in suppressing splenomegaly, in T cell and B cell proliferation, in enhancement of Th1 type cytokines (e.g. IFNγ) and in down-regulating levels of Th2 type cytokines (e.g. IL-4 and IL-6).

Accordingly, the present invention provides dimers and highly dimerised peptide preparations which may be used to treat a variety of diseases and disorders. The preparations of the present invention may be employed in a similar manner and in similar methods as the preparations of U.S. Pat. No. 5,911,990.

The designation β3 originally referred to the location of a peptide in a set of overlapping 16-mers mimicking the covalent sequence of the immunoglobulin domains of the T-cell receptor 0 chain YT35 (Marchalonis, J J et al. 1992. Proc. Natl. Acad. Sci. USA 89, 3325-3329). The numeral '3' is merely a "place name" with the β chain sequence starting with the N-terminus of the Vβ sequence and constructing sequential overlapping peptides as stated here.

The dimers of the invention have been found to normalize the functional balance between Th1 and Th2 type T cells. The preparations of the invention may be used to treat patients in which one or more of the following would provide clinical benefit: an increase in Th1 immunity; a decrease in Th2 immunity; or an improvement in general immune competence.

Thus, administration of the dimers would be expected to have a beneficial effect in patients suffering from an allergy where the pathological reactions are driven by Th2 type cytokines resulting in the generation of IgE antibodies and subsequent allergic responses. In addition, an elevation of Th1 type activity would be expected to be beneficial in facilitating immune responses to cancers, and to infectious agents, such as *Listeria*, and *Mycobacteria*, where Th1 type immunity has been shown to protect the host and Th2 type responses have been shown to support infection by the parasites. Further uses include the treatment of patients suffering from auto-immune diseases, cardiac complaints and immunosenescence. The preparations of the invention may also be used as an adjuvant, and may, for example, be used in a flu vaccine or other vaccine.

A first aspect of the present invention provides a homodimer comprising two peptide monomers, each monomer consisting of, from the N-terminus to the C-terminus direction, the sequence Cys Lys Pro Ile Ser Gly His Asn Ser Leu Phe Trp Tyr Arg Gln Thr (SEQ ID NO:1) with the proviso that, if the sequences are present as an aqueous solution, then at least 81% of the occurrences of the sequence are present as a dimer (giving a greater than or equal to 40.5:19 dimer: monomer ratio).

In addition to the peptide sequence set forth above (namely the β3 peptide of the T-cell receptor β chain clone YT35 (Yanagi, Y., et al., 1984, Nature (Ldn) 308: 145-149), herein referred to as the "β3 peptide"), various homologs of the sequence may be employed in the present invention. We have found that homologs of the peptide sequence corresponding to the same segment of other distinct human Vβ genes have immunomodulatory effects comparable to those shown by the "β3 peptide".

The definitive characteristics of the peptides of the invention are an N-terminal cysteine (C) and a tryptophan (W) at the position numbered 12 in the sequence. In this segment, residues 2-11 form the first complementary determining region (CDR1) of the human Vβ gene family. There is a minor length polymorphism of one residue in comparisons among the entire Vβ set which would put the W at position 13 in some variants. All of the translated protein products of intact human Vβ genes contain the segment defined in this manner that are homologous to the β3 peptide. The differences among members of the individual families lie in the amino acids at individual positions between 2 and 11 (12).

Thus, a second aspect of the invention provides a homodimer comprising two peptide monomers, each monomer being a homolog of the β3 peptide, wherein the homolog has the sequence of a segment of another distinct human Vβ gene which segment corresponds to the same segment as the β3 peptide. Suitably, the homolog has an N-terminal cysteine (C) residue and a tryptophan (W) residue at amino acid position 12 or 13. Optionally, the second aspect of the invention is subject to the proviso that if the sequences are present as an aqueous solution, then at least 81% of the occurrences of the sequence are present as a dimer (giving a greater than or equal to 40.5:19 dimer:monomer ratio).

In one embodiment of the second aspect of the invention, there is provided a peptide derived from the Vβ 5.2 gene product. Such a peptide and the "β3 peptide" are shown in the alignment below:

```
                    5          10         15
Pep β3      C K P I S G H N S L F W Y R Q T  Monomer
            (SEQ ID NO: 1)

(pep β3)2   C K P I S G H N S L F W Y R Q T  Dimer
            |
            C K P I S G H N S L F W Y R Q T
            (SEQ ID NO: 1 and SEQ ID NO: 1)

Pep Vβ5.2   C S P K S G H D T V S W Y Q Q A  Active
            (SEQ ID NO: 2)                   homolog
```

Variants of the β3 peptide and variants of homologs of the β3 peptide (eg the β5.2 peptide) may also be employed in the present invention. Thus, a third aspect of the invention provides a homodimer comprising two peptide monomers, the monomers being variants of a peptide sequence according to aspect 1 or 2 of the invention. Optionally, the second aspect of the invention is subject to the proviso that if the sequences are present as an aqueous solution, then at least 81% of the occurrences of the sequence are present as a dimer (giving a greater than or equal to 40.5:19 dimer:monomer ratio).

A "variant" refers to a peptide wherein at one, two, three, four, five, six, seven, eight, nine, ten or more positions there have been amino acid insertions, deletions, or substitutions, either conservative or non-conservative. Accordingly, variants include slightly longer or shorter versions of the peptides. Preferably, the changes result in a peptide having therapeutic properties, namely the modulation or alteration of the immune system, that have not been significantly impaired by the changes.

By "conservative substitutions" is intended combinations such as Gly, Ala; Val, Ile, Leu; Asp, Glu; Asn, Gln; Ser, Thr; Lys, Arg; and Phe, Tyr. Such variants may be made using the methods of protein engineering and site-directed mutagenesis.

In one embodiment, further amino acids may be linked to the β3 peptide or to a homolog thereof (eg the β5.2 peptide) by peptide bonds to one or both of the terminals of the constituent peptide sequences. Preferably, such further amino acids do not exceed 10, 5, 2 or 1 at each such terminal.

In a fourth aspect of the invention, there is provided a heterodimer comprising two peptide monomers, each of the monomers being a monomer as described in any one of the first, second or third aspects of the invention. Optionally, the fourth aspect of the invention is subject to the proviso that, if the sequences are present as an aqueous solution, then at least 81% of the occurrences of the sequences are present as a dimer (giving a greater than or equal to 40.5:19 dimer:monomer ratio).

Thus, the dimerised peptides of the invention may comprise: two β3 peptides; one β3 peptide and one homolog of the β3 peptide; two homologs of the 133 peptide; one β3 peptide and a variant of the β3 peptide; one β3 peptide and a variant of a β3 peptide homolog; two β3 peptide variants; two peptides which are variants of a β3 peptide homolog; a variant of the β3 peptide and a variant of a β3 peptide homolog; a variant of the β3 peptide and a β3 peptide homolog; a variant of a β3 peptide homolog and a β3 peptide homolog.

So that dimers may form, each of the monomers should comprise a cysteine residue at one of its termini.

In one embodiment of the invention there is a provided a preparation comprising one or more types of homodimer and alternatively or additionally one or more types of heterodimer.

Preferably, in the stated provisos of the first, second, third and fourth aspects of the invention, at least 82%, 83%, 84%, 85%, 88%, 90%, 92%, 95%, 98%, 99%, 99.5%, 99.9%, 99.99% or 99.999% of the occurrences of the sequences are present as a dimer.

One embodiment of the invention provides highly dimerised peptide compositions in which at least 81% of the peptide molecules are in the form of a dimer, preferably, at least 82%, 83%, 84%, 85%, 88%, 90%, 92%, 95%, 98%, 99%, 99.5%, 99.9%, 99.99%, 99.999% or substantially 100% of the peptide molecules being in the form of dimers.

At pHs of about pH 4.5 or higher, spontaneous dimerisation of the cysteine-containing peptide sequences is favoured through the formation of a disulphide bond. In principle any pH of 4.5 or above should work.

However, at very high pHs (greater than 9.5) the peptides would be predisposed to denaturation and proteolysis. Preferably, the peptides are dimerised at a pH of at least pH 4.5, pH 5.0, pH 5.5, pH 6.0, pH 6.5, pH 7.0, pH 7.5, pH 8.0, pH 8.5, pH 9.0, or pH 9.5. Preferably, the peptides are dimerised at a pH less than any one of the following pHs: pH 10.5, pH 10, pH 9.5, pH 9, pH 8.5, pH 8 or pH 7.5. In a more preferred embodiment peptides are dimerised at a pH of from pH 4.5 to pH 7.5, even more preferably at a pH of from pH 5.0 to pH 7.0. The most preferred pH is pH 5.0.

Dimerisation is also favoured by high peptide concentrations. The higher the peptide concentration the higher the percentage dimerisation. At or above a critical peptide concentration substantially 100% dimerisation can be achieved. At a reasonable concentration; e.g. greater that 1 mg/ml, the reaction should go to completion given sufficient time (hours).

In principle, the procedure for making the dimerised peptide preparations of the invention consists of allowing the spontaneous dimerization to occur and separating the dimer from residual monomer by high performance liquid chromatography (HPLC). These are routine steps in peptide chemistry and the product used in the studies described herein is synthesized commercially by American Peptide Inc., using standard technology.

Dimerization of two monomers may also be achieved through a peptide bond. The terms "dimer", "homodimer" and "heterodimer" are also intended to include a single polypeptide comprising an amino acid sequence that is equivalent to a "dimer", "homodimer" or "heterodimer" of the first, second, third or fourth aspect of the invention. For example, reference to a "homodimer" of a first aspect of the invention includes within its meaning a polypeptide consisting of, from the N-terminus to the C-terminus, the sequence Thr Gln Arg Tyr Trp Phe Leu Ser Asn His Gly Ser Ile Pro Lys Cys Cys Lys Pro Ile Ser Gly His Asn Ser Leu Phe Trp Tyr Arg Gln Thr (SEQ ID NO:3). It will be clear to the skilled person that, whilst the primary amino acid sequence of the single polypeptide equivalent can be identical to a dimer, homodimer or heterodimer, the peptide bond orientation in relation to the amino acids of the region equivalent to one of the monomers will be in reverse. This may be avoided by using retro-inverso peptidomimetics, described in more detail below. Using these strategies it is possible to produce polypeptide preparations wherein substantially 100% of the occurrence of the monomer sequences are in the form of dimers. Moreover, this can be achieved without the need for conditions that favour dimerization of the monomers.

Persons skilled in the art will appreciate that alternative methods may be used to prepare the dimerised peptides of the present invention.

By "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Mézière et al (1997) J. Immunol. 159, 3230-3237, incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis.

Alternatively, the peptide bond may be dispensed with altogether provided that an appropriate linker moiety which retains the spacing between the Cα atoms of the amino acid residues is used; it is particularly preferred if the linker moiety has substantially the same charge distribution and substantially the same planarity as a peptide bond.

Peptides in which one or more of the amino acid residues are chemically modified, before or after the peptide is synthesised, may be used providing that the biological activity of the peptide, namely the modulation or alteration of the immune system, is not significantly impaired. Such modifications include forming salts with acids or bases, especially physiologically acceptable organic or inorganic acids and bases. Also, the peptide may be blocked at its N- or C-terminus. Such modifications may protect the peptide from in vivo metabolism.

The peptides may be associated, for example by cross-linking, with a separate carrier, such as serum albumins, ovalbumin, myoglobins, bacterial toxoids, keyhole limpet haemocyanin, or other native or engineered proteins. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys (SEQ ID NO:4, β-galactosidase and the 163-171 peptide of interleukin-1. The latter compound may variously be regarded as a carrier or as an adjuvant or as both.

Whilst it may be possible for the dimerised peptides of the invention to be presented in raw form, it is preferable to present them as a pharmaceutical formulation. Suitably, the pharmaceutical formulation comprises one or more pharmaceutically acceptable excipients, carriers or diluent.

A fifth aspect of the invention provides dimerised peptides of the first, second, third and fourth aspects of the invention packaged and presented for use in medicine. Suitable ingredients for presenting the dimerised peptides of the invention are described below.

Preferably, the dimerised peptides will be packaged with an indication of who may be treated (in particular who may benefit from being treated). Further, it is preferred that the peptides of the composition is packaged and presented with an indication of the dose which is to be used and/or how often the preparation is to be administered and/or the preferred route of administration.

A sixth aspect of the invention relates to the use of the dimerised peptides of the first, second, third and fourth aspects of the invention in the manufacture of a medicament for modulating or altering the immune response of an animal.

Preferably, the dimerised peptides are presented in combination with one or more pharmaceutically acceptable carriers. Carriers are well known in the art and include keyhole limpet haemocyanin (KLH) and mannan (see WO95/18145 and Longenecker et al (1993) Ann. NY Acad. Sci. 690, 276-291). The carrier(s) must be 'acceptable' in the sense of being compatible with the other ingredients of the formulation and not deleterious to the recipient thereof. Typically, carriers for injection, and the final formulation, are sterile and pyrogen free.

The preparations of the present invention may further comprise an immune-stimulating adjuvant. Suitable adjuvants include Detox, Freund's complete or incomplete adjuvant, muramyl dipeptide, poly (AU), the Iscoms of EP 109 942, EP 180 564 and EP 231 039, aluminium hydroxide, saponin, DEAE-dextran, neutral oils (such as miglyol), vegetable oils (such as arachis oil), liposomes, Pluronic polyols or the Ribi adjuvant system (see, for example GB-A-2 189 141). The preparations of the invention may also comprise (or be used in combination with) immune-stimulatory cytokines.

In one preferred embodiment the preparations of the present invention comprise one or more of: a sugar alcohol (eg mannitol), sterile water, phosphate buffer sterile water, and an adjuvant, preferably Freund's incomplete adjuvant.

The preparations of the invention may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Preparations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropyl-methylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above the preparations of this invention may include other agents conventional in the art having regard to the type of formulation in question, for example those suitable for oral administration may include flavouring agents. Further, as discussed below, the preparations of the invention may comprise one or more additional therapeutic agents.

In one embodiment, the additional therapeutic agent is a peptide. Examples of peptides which may usefully be combined with the preparations of the invention include peptides involved in vaccination against tumors, eg Mage1, Mage2 and other peptides involved in the T-cell mediated destruction of melanoma antigens (Kawakami, Y. and Rosenberg, S. A. (1997) Human tumor antigens recognized by T-cells. *Immunol. Res.* 16:313; and Boom, T. (1993) Tumor antigens recognized by cytolytic T lymphocytes: present perspectives for specific Immunotherapy. *Int. J. Cancer* 54:177).

The components of the composition may be mixed together in a form ready for administration, or they may be present separately for sequential or simultaneous administration. In the latter case, the preparations of the invention could be considered to be a package of medicines or a kit of parts.

A seventh aspect of the present invention provides a method of modulating or altering the immune response of an animal using a preparation of the invention.

The theory underlying the TCR Vβ CDR1 peptide administration approach of the invention is that the preparations of the invention should be beneficial in any situation (eg infectious, autoimmune, or environmental) in which autoantibodies against the family of TCR Vβ CDR1 peptides are generated.

In a preferred embodiment of the present invention, immunosuppression and/or abnormal cytokine production is prevented or reversed. In one embodiment, production of Th1 cytokines (eg interleukin 2, interferon-γ) is stimulated and/or production of Th2 cytokines (eg interleukin 5, interleukin 6, interleukin 10) is suppressed. Advantageously, normal levels of immunoglobulin G are restored.

Accordingly, the preparations of the invention may be used to treat patients in which one or more of the following would provide clinical benefit: an increase in Th1 immunity; a decrease in Th2 immunity; or an improvement in general immune system competence. An improvement in immune system competence may, for example, be measured by the ability of the immune system to respond to pathogens and/or by the strength of that response.

The preparations of the invention are believed to have a similar qualitative therapeutic effect as the peptides of U.S. Pat. No. 5,911,990. Thus, the preparations of the invention may be efficacious in infectious diseases where Th1 type immunity and/or NK function are beneficial. Examples of such diseases are leishmaniasis, tuberculosis and leprosy.

With respect to the role of Th1 type immunity and/or NK function in leishmaniasis, see: Infante-Duarte, C., Kamradt, T. Th1/Th2 balance in infection. Springer Semin. *Immunopathol.* 21(3):317-338, 1999; Lohoff, M., Gooanor, A., Bogdan, C., Rollinghoff, M. Experimental murine leishmaniasis and the Th1/Th2 cell concept. *Tokai J. Exp. Clin. Med.* 23(6):347-50, 1998; Rocha, P. N., Almeida, R. P., Bacellar, O., de Jesus, A. R., Filho, D. C., Filho, A. C. Banal, A., Coffman, R. K. Carvalho, E. M. Down-regulation of Th1 types of response in early human American cutaneous leishmaniasis. *J. Infect. Dis.* 180(5):1731-1734, 1999; Kenney, R. T., Sacks, D. L., Sypek, J. P., Vilela, L., Gam, A. A., Evans-Davis, K. Protective immunity using recombinant human IL-12 and alum as adjuvants in a primate model of cutaneous leishmaniasis. *J. Immunol.* 163(8):4481-4488, 1999; Akuffo, H., Alexis, A., Eldsmo, L., Saed, A., Nylen, S., Maasho, K. Natural killer cells in cross-regulation of IL-12 by IL-10 *Leishmania* antigen-stimulated blood donor cells. *Clin. Exp. Immunol.* 117(3):529-534, 1999;

With respect to the role of Th1 type immunity and/or NK function in tuberculosis, see: Infante-Duarte, C., Karnradt. T. Th1/Th2 balance in infection, Springer Semin. *Immunopathol.* 21(3):317-338, 1999; and Hirsch, C. S., Toossi, Z., Othiona, C., Johnson, J.L., Schwander, S.K., Robertson. S., Wallis, R.S., Edmonds, K., Okware, A., Mugerwa, R., Peters, P., Ellner, J. J. Depressed T cell interferon gamma responses in pulmonary tuberculosis: analysis of underlying mechanisms and modulation with therapy. *J. Infect. Dis.* 180(6): 2069-2073. 1999.

With respect to the role of Th1 type immunity and/or NK function in leprosy, see Aleman, M., De la Barrera, S, Fink, S., Finiasz, M. Farina, M. H., Pizzariellow, G. Sasiain, M.D. Interleukin-12 amplifies the *M. teprae* hsp65-cytotoxic response in the presence of tumour necrosis factor-alpha and interferon gamma generating CD56+ effector cells: interleukin-4 downregulates this effect. *Scand. J. Immunol.* 51(3): 262-270, 2000; Moraes, M. O. Sarho, E.N., Almeida, A.S., Saraiva, B.C., Nery, J.A., Martins, R. C., Sampalo, F. P., Cytokine mRNA expression in leprosy: a possible role for interferon-gamma and interleukin-12 in reactions (RR and ENL). *Scand. J. Immunol.* 50(5):541-549, 1999; Mitra, D. K., De Rosa., S. C., Luke, A., Balamurugan, A., Khaltan, B. K., Tung, J., Mehr, N. K., Terr, A. L., O'Garra, A., Herzenberg, L. A., Roederer, M. Differential representations of memory T cell subsets are characteristic of polarized immunity in leprosy and atopic diseases, *Int. Immunol.* 11(11): 1801-1810, 1999; Garcia, V. E., Uymura, K., Sieling, P. A., Ochoa, M. T., Morita, C. T., Okamura, H., Kurimoto, M., Rea, T. G., Modlin, R. L., IL-18 promotes type 1 cytokine production from NK cells and T cells in human intracellular infection. *J. Immunol.* 62(10): 6114-6121, 1999.

Liang, B., Marchalonis, J. J., and Watson, R. R. (1997) Prevention of immune dysfunction, vitamin E deficiency and loss of *Crytosporidium* resistance during murine retrovirus infection by T cell receptor peptide immunization. *Nutr. Res.* 17:677-692), indicates the efficacy of the peptide monomers of U.S. Pat. No. 5,911,990 in reestablishment of resistance of mice to infection with the opportunistic parasite *Cryptosporidium*.

The administration of the peptides of U.S. Pat. No. 5,911,990 has multiple effects on cellular immune reactions of retrovirally infected and aged mice. One aspect is the strengthening of Th1 type cell mediated immunity via re-establishing a balance of Th1/Th2 cytokine production and function. A second aspect is the enhancement of the function of natural killer (NK) cells, which play an important role in responding to infectious agents, and particularly in responding to tumours. The ability of the peptides of U.S. Pat. No. 5,911,990 to modulate their appearance and function illustrates its profound interaction with members of the cytokine mediated cellular immune network incorporating NK cells, phagocytic cells, and T-cells. For example, NK cells can be activated to secrete INF-γ (a major Th1 type cytokine) by interleukin-12. Furthermore, IL-4 and IL-3 are structurally related and induce IgE production by human B cells.

The dimerised peptide preparations of the present invention are expected to be efficacious in situations where Th1 type, and NK cell and other T cell mediated cellular immunity is required, which is the case with many infectious diseases. Allergies and asthma represent the opposite situation because the pathology is mediated by the effects of the reaginic antibody IgE that is induced by Th2 type cytokines, notably IL-4 and IL-13. The deleterious effect of Th2 type cytokines on increasing the prevalence or severity of allergy and asthma are documented in the following publications: Moveare, R., Elfinan, L. Moverare, R., Stalenheim, G., Bjornsson, E. Study of the Th1/Th2 balance, including IL-10 production, in cultures of peripheral blood mononuclear cells from birch-pollen-allergic patients. *Allergy* 55(2) 171-175, 2000; Kimura, M. Tsurtua, S., and Yoshida, T. IL-4 production by PBMCs on stimulation with mite allergen in correlated with the level of serum IgE antibody against mite in children with bronchial asthma. *J. Allergy Clin. Immunol.* 105(2 Pt1) 327-332. 2000; and Yssel, H., Groux, H. Characterization of T cell subpopulations involved in the pathogenesis of asthma and allergic diseases. *Int. Arch. Allergy Immunol.* 121(1): 10-18, 2000.

Examples of infections which may be treated with the preparations of the invention include viral and non-viral pathogens. Viral pathogens include C-type retroviruses (MULV/MAIDS), lentiviruses (HIV including HIV-1, HIV-2, and HIV-3, simian immunodeficiency virus (SIV), and feline immunodeficiency virus (FIV)).

In one embodiment of the present invention, the deleterious effects of an immunodeficiency-type retrovirus, preferably HIV, are prevented or reversed. Accordingly, preparations and methods are provided that are useful in preventing or reversing retrovirus-induced suppression of immune responses and normalizing cytokine production in an animal infected with an immunodeficiency-type retrovirus. More specifically, the present invention provides preparations and methods useful in delaying the onset of AIDS.

U.S. Pat. No. 5,911,900 discusses changes in the immune system brought about by TCR Vβ CDR1 peptide administration, and also possible mechanisms that may be responsible for prevention of immune dysfunction during immunodeficiency-type retrovirus infection and concomitant TCR Vβ CDR1 peptide administration.

The changes in retrovirus-induced immune dysfunction and cytokine production in the animal following administration of the TCR Vβ CDR1 peptide occur simultaneously with restoration of tissue vitamin E, a mild immunostimulant and reduced lipid peroxidation in tissues, which decreases the oxidative stress caused by free radical products, i.e., lipid fluorescence and diene conjugates.

Non-viral pathogenic diseases may also be treated with the preparations of the invention. Non-viral pathogenic diseases include protozoal infections, bacterial infections and fungal infections (eg coccidomycosis).

In one embodiment the preparations of the invention may be used to treat Leishmaniasis. This disease is a group of infections caused by flagellate protozoan parasites of the genus *Leishmania* spp. Cutaneous leishmaniasis is caused by infection with *L. tropica, L. major, L. aethiopica*, and other species. Mucocutaneous leishmaniasis is caused by *L. braziliensis* and rarely *L. mexicana*.

In another embodiment the preparations of the invention may be used to treat leprosy (Hansen's disease). Examples of the disease include lepromatous (multi-bacillary) leprosy, tuberculoid leprosy, indeterminate leprosy and paucibacillary leprosy.

In another embodiment the preparations of the invention may be used to treat infection with *Coccidioides immitis* (Valley Fever). *Coccidioides immitis* travels through the air in dust particles into the lungs, where it may grow and spread to other body regions. In susceptible people, the fungus can cause pneumonia or lumps in the lungs that may be mistaken for lung cancer. Left untreated, the fungus sometimes spreads to the skin and bones or, rarely, leads to meningitis. A significant number of patients suffer nervous system involvement, a very chronic, difficult-to-manage condition, often including dementia.

People who are most prone to these complications are those undergoing chemotherapy or long-term corticosteroid treatment; women in the third trimester of pregnancy; and people who have diabetes, AIDS, or have had an organ transplant.

In addition to humans, many domestic and native animals are susceptible to the disease, including dogs, horses, cattle, sheep, burros, coyotes, rodents, bats and snakes. Accordingly, the preparations to the present invention may not only find application in treating humans but also in treating animals suffering from *Coccidioides immitis* infection or any other disorder in which an increase in Th1 immunity, a decrease in Th2 immunity, or an improvement in general immune competence may be beneficial.

In addition to infectious diseases, the preparations of the invention may be used to treat a variety of other disorders. In one embodiment of the invention, the preparations of the invention may be used to treat an auto-immune disease. Examples of autoimmune diseases include rheumatoid arthritis, Crohn's disease, insulin-dependent diabetes mellitus, multiple sclerosis (MS), atherosclerosis, Hashimoto's thyroiditis, coeliac disease, myasthenia gravis, pemphigus vulgaris; systemic lupus erythematosus (SLE), Grave's disease and systemic vasculitis. Auto-immune diseases which affect non-human mammals include experimental allergic encephalomyelitis (EAE), which is a much studied animal model for MS.

The preparations of the invention may be used to treat patients who have come into contact with environmental agents, such as oils and adjuvants, that amplify various features of the immune system. A beneficial effect of the peptides of the invention would be expected if the environmental agent diminishes Th1 type cellular immunity.

In another embodiment of the invention, the preparations of the invention may be used to treat an allergic disease, for example asthma, allergic rhinitis (seasonal or perennial) and atopic dermatitis.

Administration of the dimers of the present invention can be used to enhance Th1 type immunity in the cancer patients. Accordingly, in another embodiment, the preparations of the invention may be used to treat cancer. Suitably, the cancer patient is immunocompromised, preferably by chemotherapy.

The peptides of the invention would be effective in the treatment of cancers to which cellular immune responses confer protection on the host. Among these are melanomas and breast cancers. In addition, because of its effect on diminishing lymphoid hyperplasia in retrovirally infected animals, it would be expected to decrease the incidence of lymphoid tumors in retroviral infections or in other circumstances where the host immune response tends to be immunosuppressed.

In yet another embodiment, the preparations of the invention may be used to treat cardiac patients. In one embodiment the preparations of the invention may be used to diminish negative consequences of infection by viruses, such as Coxsackie virus, that cause inflammatory heart disease, particularly in individuals that are immunosuppressed because of HIV infections.

The preparations of the invention may also serve as an adjuvant and may, for example, be used in a flu vaccine or other vaccine.

Previous studies have indicated that immune dysfunction and abnormal cytokine production induced by the ageing process can, at least in part, be prevented or reduced by injection of selected TCR Vβ CDR1 peptides. TCR Vβ CDR1 peptides have been shown to retard the excessive production of IL-4, IL-6, and TNF-α induced by ageing. See for example Liang et al. (1998), *Immunology* 93: 462-468. Liang et al. discloses that injection of peptides having the sequence Cys Lys Pro Ile Ser Gly His Asn Ser Leu Phe Trp Tyr Arg Gln Thr (SEQ ID NO:1) (ie the peptides which are used in the present invention, albeit not "highly dimerised") reduces immunosenescence in aged mice. Accordingly, in one embodiment the preparations of the invention are used to treat immune dysfunction and abnormal cytokine production induced by the ageing process. In particular, the preparations of the invention may be used to enhance Th1 type immunity.

The cellular molecular basis of immunosenescence is extremely complex but cytokine imbalances occur that raise the possibility that the preparations of the invention should be efficacious in treating immunosenescence. References consistent with this position are as follows: Jolly, C. A., Fernandez, R., Muthukumar, A. R., Fernandes, G, Calorio restriction modulates Th-1 an Th-2 cytokine-induced immunoglobulin secretion in young and old C57BL/6 cultured submandibular glands. *Aging (Milano)* 11(6): 383-389, 1999; Albright, J. W., Albright, J. F., Soluble receptors and other substances that regulate proinflammatory cytokines in young and aging humans. *J. Gerontol. A. Biol. Sci. Med. Sci.* 55(1):B20-25, 2000; Solana, R., Mariani, E. NK and NK/T cells in human senescence. *Vaccine* 18(16):1613-1620, 2000; Karanfilov, C. I., Llu, B., Fox, C. C., Lakshmanan, R. R. and Whisler, R. L. Age-related defects in Th1 and cytokine production by human T cells can be dissociated from altered frequencies of CD45RA+ and CD45RO+ T cell subsets. *Mech. Ageing Dev.* 109(2):97-112, 1999; Fermandez-Gullerrez, B., Jover, J. A., De Miguel S., Hernandez-Garcia, C., Vidan, M. T. Ribera, J. M. Banaers, A., Serra, J. A. Early lymphocyte activation in elderly humans: impaired T and T-dependent B cell responses. *Exp. Gerontol.* 34(2): 217-229, 1999; Timm, J. A., Thoman, M. L. Maturation of CD4+ lymphocytes in the aged microenvironment results in a memory-enriched population. *J. Immunol.* 162(2):711-717, 1999; and Castle, S., Uyomura, K., Wong, W., Modin, R., and Effroe, R. Evidence of enhanced type 2 immune response and impaired upregulation of a type 1 response in frail elderly nursing home residents. *Mech. of Ageing & Devel.* 94:7-16, 1997. Also, Llang, B., Zhang, Z., Inserra, P., Jiang, S., Lee, J., Garza, A., Marchalonis, J. J. and Watson, R. R. Injection of T-cell receptor peptide reduces immunosenescence in aged C57BL/6 mice. *Immunology* 93:462-568, 1998, indicates the efficacy of administration of the monomeric peptides of U.S. Pat. No. 5,911,990 in mice with diminished immune capacity because of aging.

One embodiment of the invention provides a preparation of the invention which comprises, in combination, but not necessarily for contemporaneous administration, one or more additional therapeutic agents.

Preferably, the additional therapeutic agent is an agent that is suited to the therapeutic needs of the patient. Preferably, the patient is suffering from one of more of the above-mentioned diseases and disorders.

In one embodiment the patient is suffering from HIV or AIDS and the therapeutic agent is useful in the treatment of HIV-infection. Acyclovir, AZT, ddI, amantadine hydrochloride, inosine pranobex, vidarabine, and the like, may be used.

Other therapeutic agents which may usefully be combined with the dimerised peptides of the invention include: antibiotics, anti-histamines or a cancer-treating agent.

When the peptides of the invention are used in combination with a further therapeutic agent which is active against the same condition as the dimerised peptides the dose of each compound may be either the same as or different from that when the compound is used alone. Appropriate doses of the peptides of the invention are discussed below.

Systemic routes that may be used for administering the preparations of the invention include intravenous injection, intraperitoneal injection, oral administration, subcutaneous administration, intramuscular administration, and administration by autologous dendritic cells.

One system for oral administration of proteins or peptides employs a natural process for oral uptake of vitamin B12 in the body to co-deliver proteins and peptides. By riding the vitamin B12 uptake system, the protein or peptide can move through the intestinal wall. Complexes are synthesised between vitamin B12 analogues and the drug that retain both significant affinity for intrinsic factor (IF) in the vitamin B12 portion of the complex and significant bioactivity of the drug portion of the complex.

The preparations of the invention may be delivered using an injectable sustained-release drug delivery system. These systems are designed specifically to reduce the frequency of injections. An example of such a system is Nutropin Depot which encapsulates recombinant human growth hormone (rhGH) in biodegradable microspheres that, once injected, release rhGH slowly over a sustained period.

An alternative method of delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The active agent is delivered over time as the biopolymers dissolve.

Treatment may consist of a single dose or a plurality of doses over a period of time. The peptides should be administered in an amount effective to have a desirable effect in the patient. Those skilled in the art will appreciate that the effective amount of peptide per unit dose will depend on, among other things, the species of animal inoculated, the body weight of the animal, the route of administration and whether the TCR Vβ CDR1 peptide is administered with or without adjuvant.

For example, for subcutaneous administration by injection, less than 1 mg/kg of body weight may be administered for the peptide therapy to be effective. Preferably, peptide administered to an animal infected with an immunodeficiency-type retrovirus should be made in at least two administrations.

Typically, doses of 5 mg/kg of body weight to 25 mg/kg of body weight of TCR Vβ CDR1 peptide in saline are administered in divided doses following infection. Preferably, doses of approximately 10 mg/kg of body weight to 25 mg/kg of body weight of TCR Vβ CDR1 peptide in saline are administered in divided doses. Most preferably, doses of about 10 mg/kg of body weight are administered. Multiple doses administered approximately once per month increase the efficacy of the TCR Vβ CDR1 peptide therapy.

Preferably one or more doses of at least 25 μg, 50 μg, 60 μg, 70 μg, 80 μg, 90 μg, 100 μg, 110 μg, 120 μg, 130 μg, 140 μg, 150 μg, 175 μg, 200 μg, 225 μg, 250 μg, or 300 μg is administered. Preferably about 50 μg, 75 μg, 100 μg, 125 μg, 150 μg, or 200 μg is administered.

Preferably, treatment is performed early, prior to significant immune dysfunction. Thus, in one embodiment the preparations of the invention are administered to an HIV patient, before the onset of AIDS.

Preferably, the patient is a mammal, preferably a human, rodent (eg mouse, rat or hamster), livestock, guinea pig, rabbit or primate. A particular group of patients who are believed to be likely to benefit from treatment with preparations of the invention, are patients with HIV infection and particularly those with acquired immune deficiency syndrome (AIDS).

Those skilled in the art will recognize that, while specific embodiments have been illustrated and described, various modifications and changes may be made without departing from the spirit and scope of the invention.

The invention will now be described in more detail with reference to the following non-limiting examples and figures.

FIG. 1. Spleen weight. The spleen weights were substantially (p<0.05) elevated in the infected mice relative to the uninfected animals. Infected animals given either monomer or dimer showed significant reduction in spleen weight relative to the untreated infected animals. The degree of suppression brought about by the monomers and dimers were not significantly different from one another. Although diminished, the spleen weights were significantly different from those of the uninfected animals. "a" indicates significant differences at p<0.05 compared with uninfected saline treatment.

Figure 2:
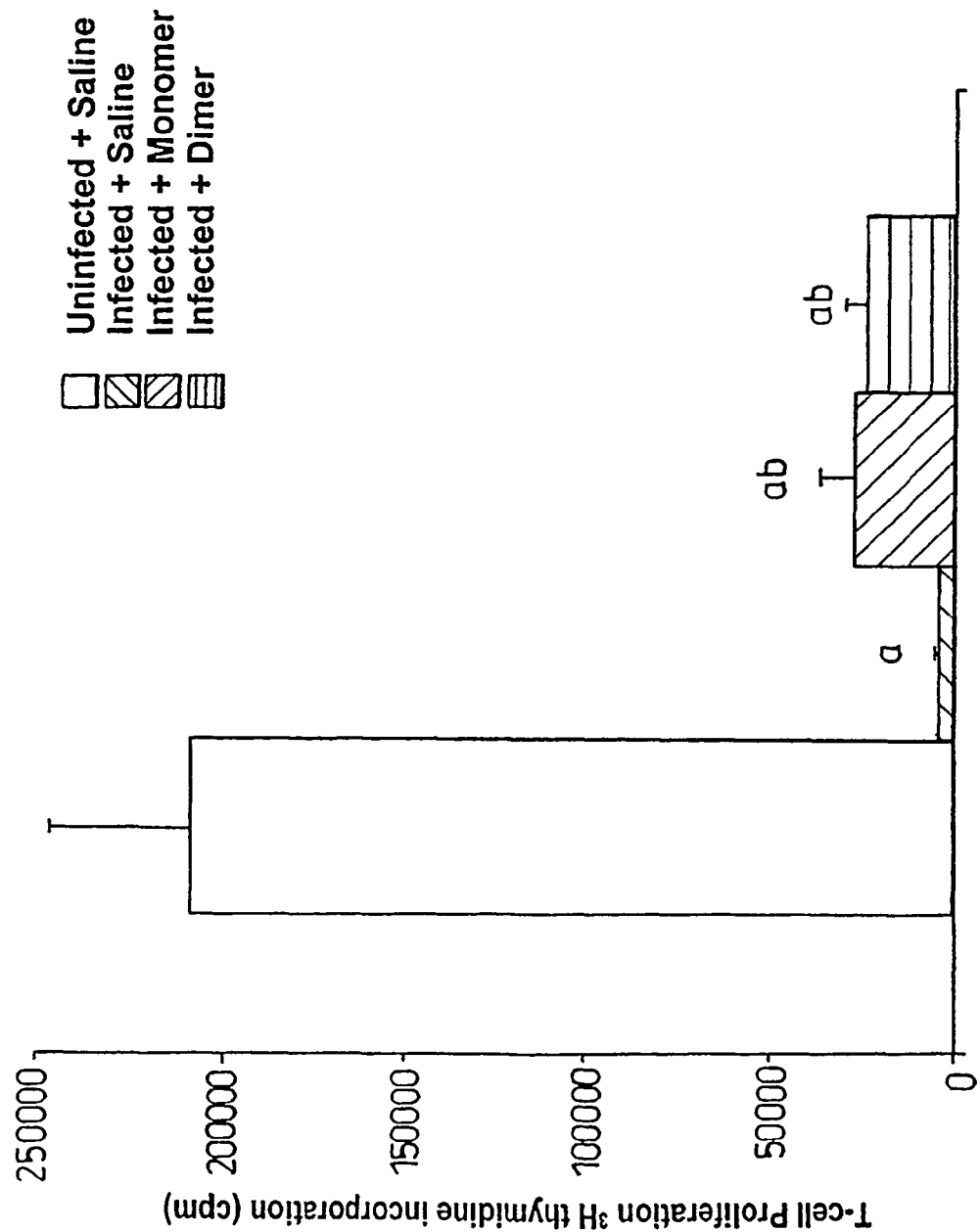

FIG. 2. Con A-stimulated splenocyte proliferation. LP-BM5 infection significantly (p<0.05) suppressed t cells proliferation. TCR Vβ3 momomer and dimer peptide treatments at doses 200 μg/mouse significantly (p<0.05) prevented the suppression of T-cell proliferation in LP-BM5 infection mice. "a" indicates significant differences at p<0.05 compared with uninfected saline treatment group. "b" indicates significant differences at p<0.05 compared with infected saline treatment group.

Figure 3:
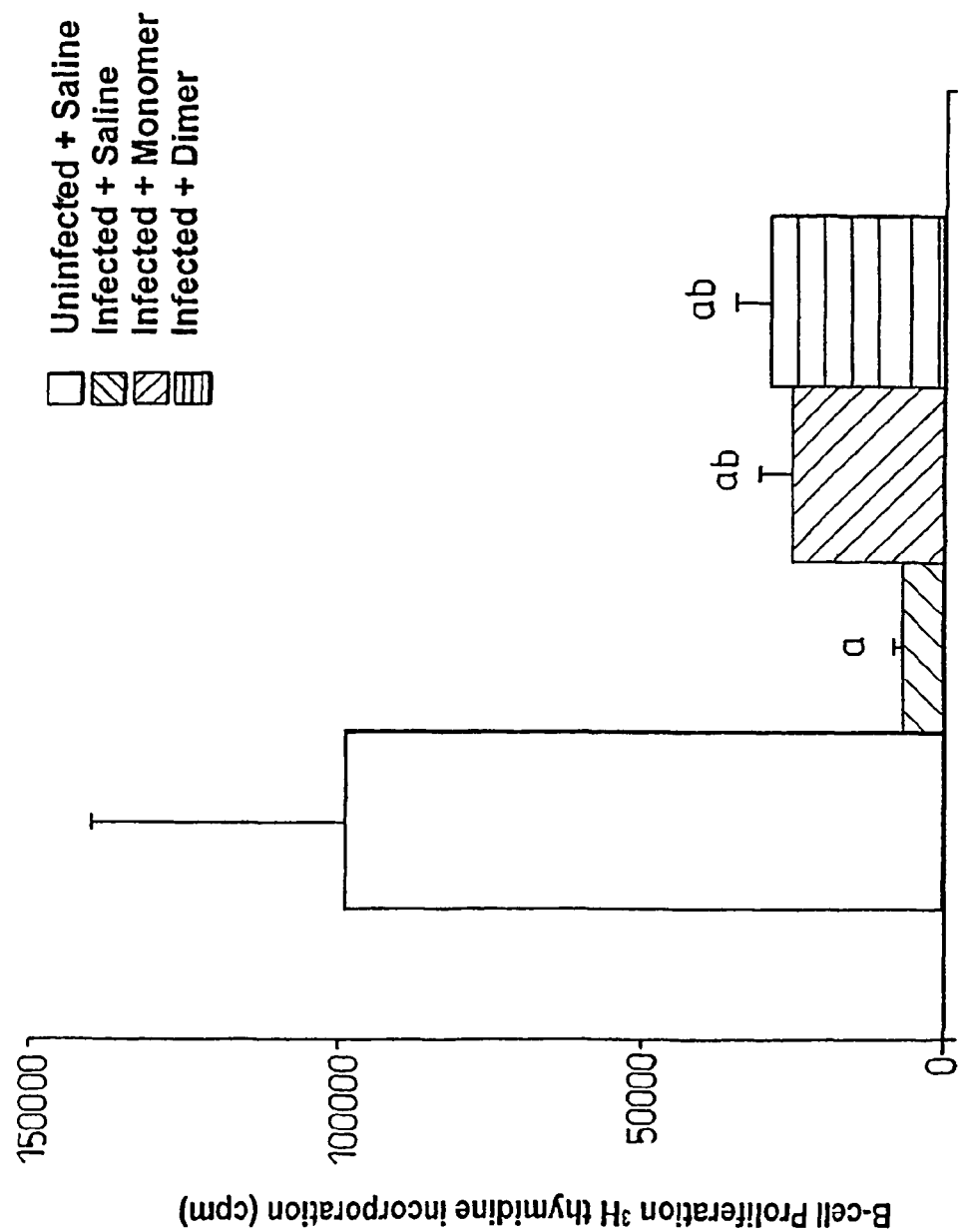

FIG. 3. LPS-stimulated splenocyte proliferation. LP-BM5 infection significantly (p<0.05) suppressed B cells proliferation. TCR Vβ3 monomer and dimer peptide treatments at doses 200 μg/mouse significantly (p<0.05) prevented the suppression of T-cell proliferation in LP-BM5 infection mice. "a" indicates significant differences at p<0.05 compared with uninfected saline treatment group. "b" indicates significant differences at p<0.0.5 compared with infected saline treatment group.

Figure 4:
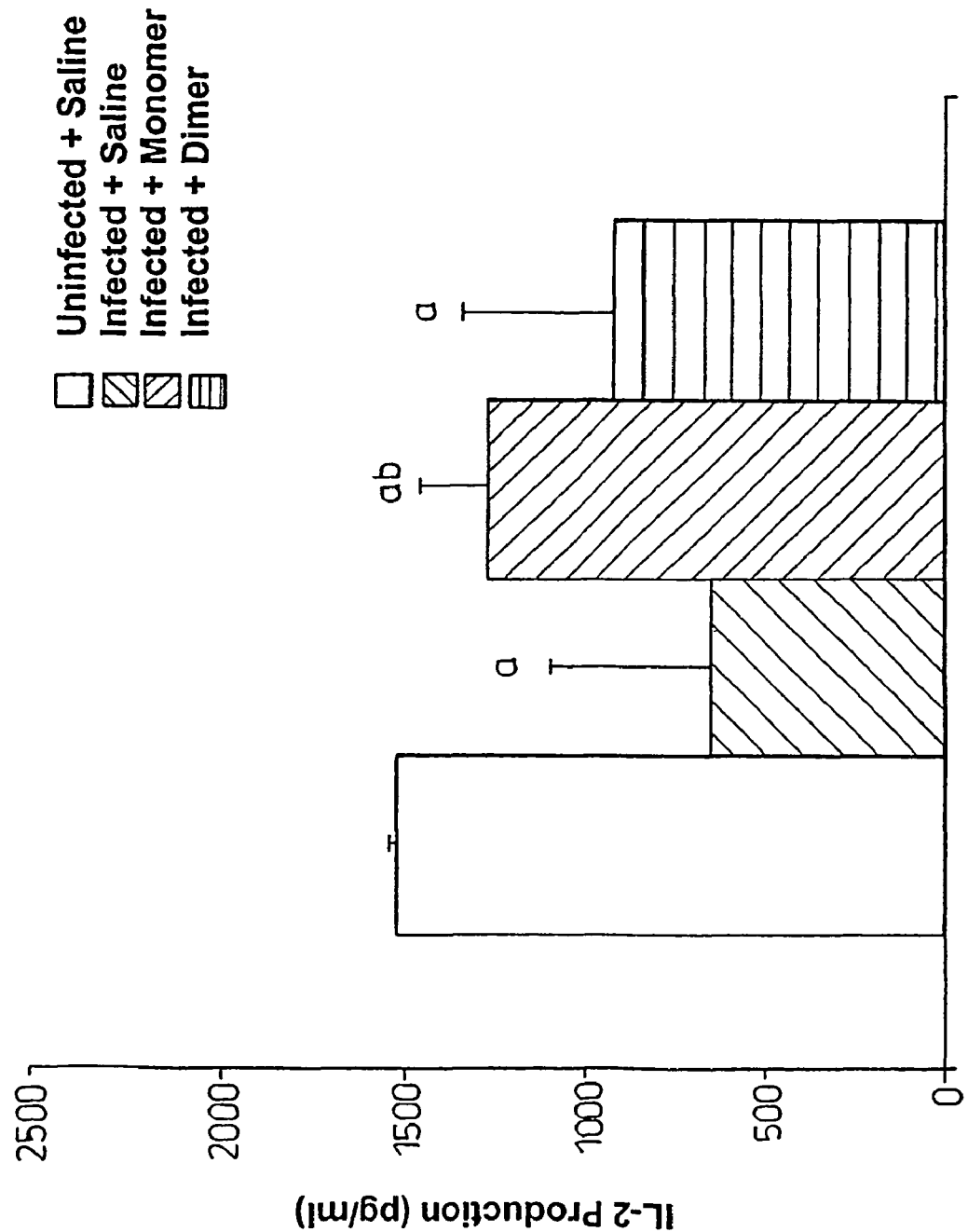

FIG. 4. IL-2 production of splenocyte. LP-BM5 infection significantly (p<0.05) suppressed IL-2 production. TCR Vβ3 monomer treatments significantly (p<0.05) normalized IL-2 production at doses 200 μg/mouse. "a" indicates significant differences at p<0.05 compared with uninfected saline treatment group. "b" indicates significant differences at p<0.05 compared with infected saline treatment group.

Figure 5:
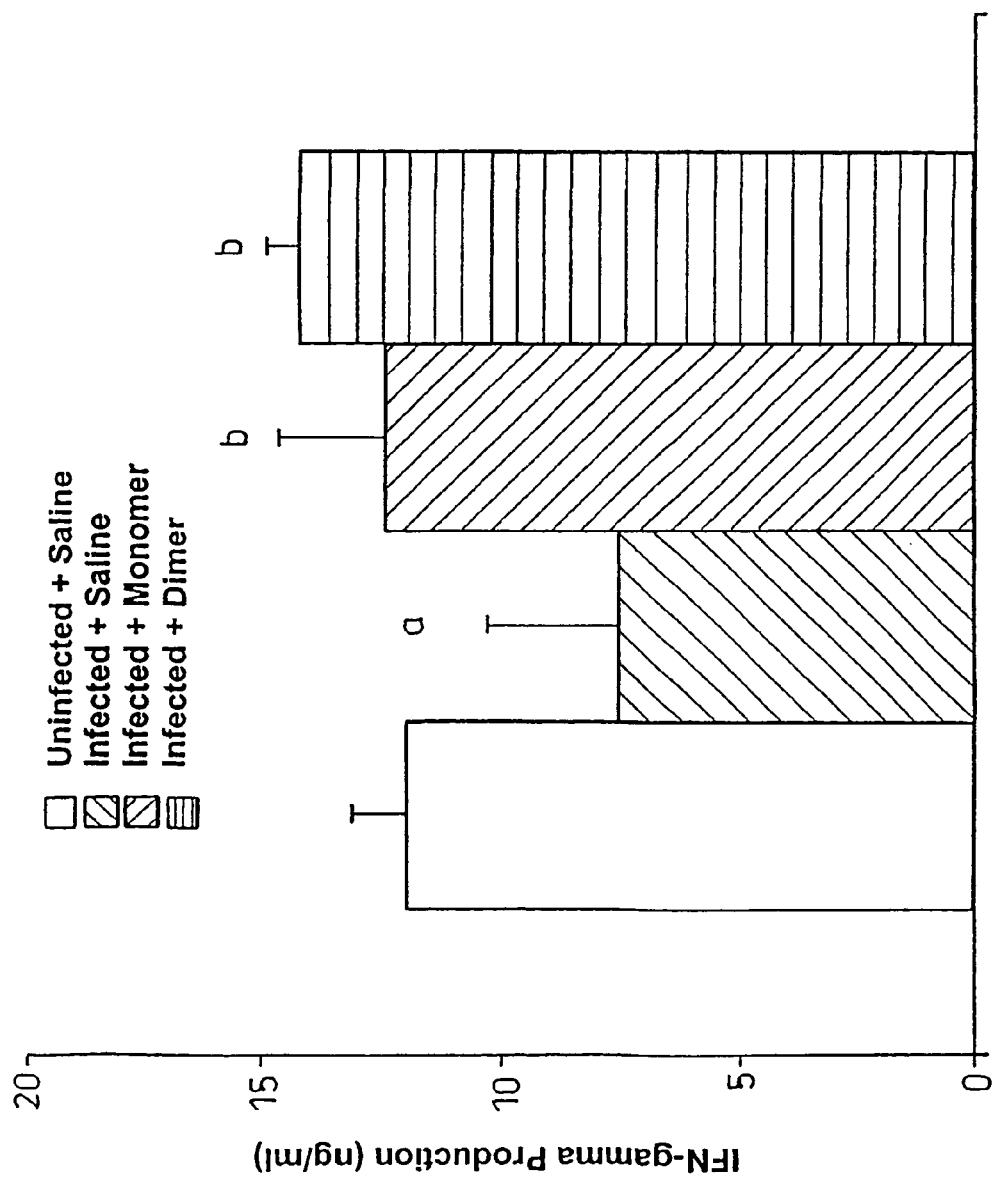

FIG. 5. IFN-γ production of splenocyte. LP-BM5 infection significantly (p<0.05) suppressed IFN-γ production. TCR Vβ3 monomer and dimer peptide treatments at doses of 200 μg/mouse significantly (p<0.05) normalized IFN-γ production. "a" indicates significant differences at P <0.05 compared with uninfected saline treatment group. "b" indicates significant differences at P<0.05 compared with infected saline treatment group.

Figure 6:
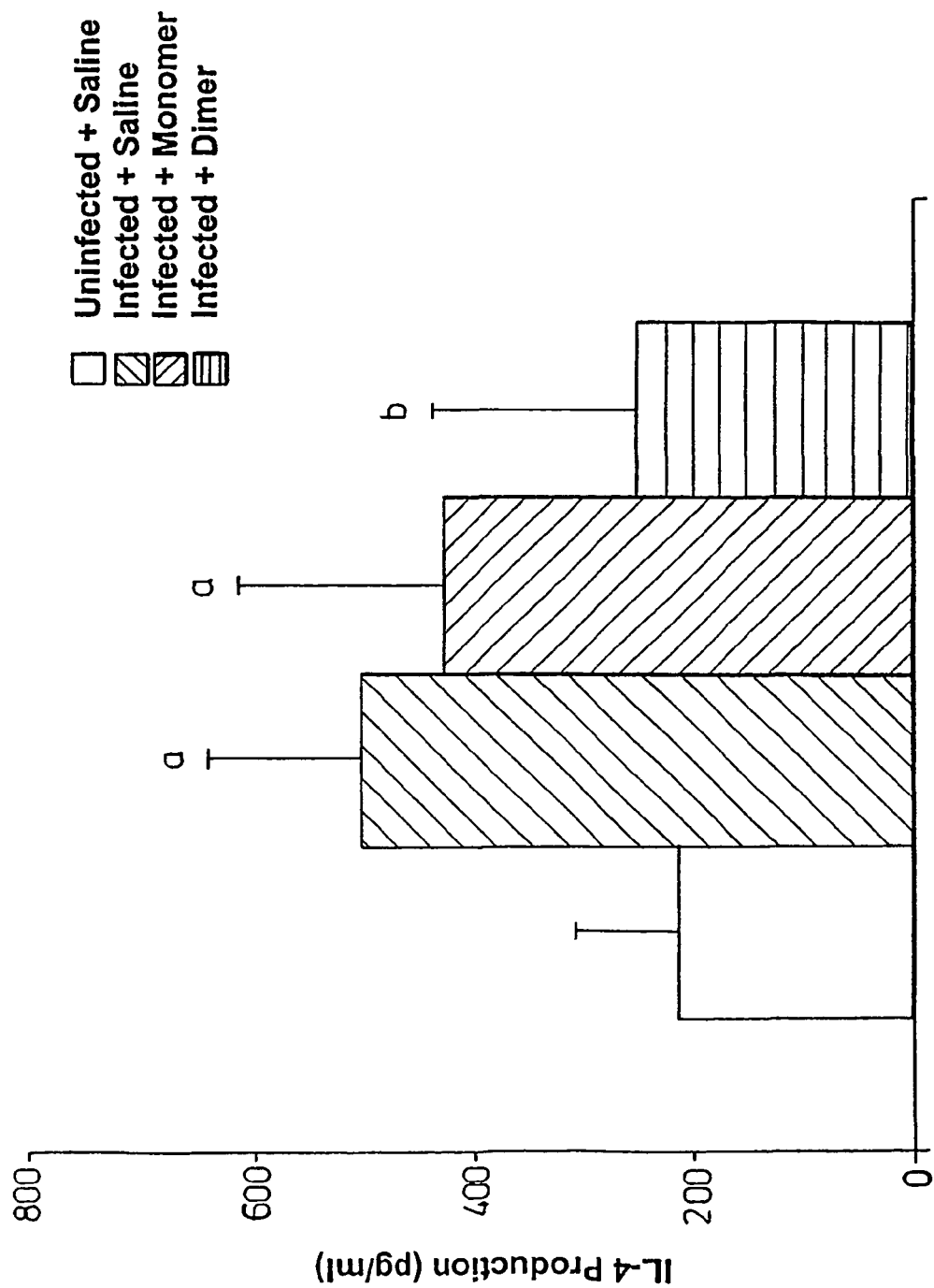

FIG. 6. Interleukin-4 production of splenocyte. LP-BM5 infection significantly (p<0.05) increased IL-4 production. TCR Vβ3 dimer treatments at doses 200 μg/mouse significantly (p<0.05) normalized IL-4 secreted by mitogen-stimulated splenocytes. "a" indicates significant differences at P<0.05 compared with uninfected saline treatment group, "b" indicates significant differences at P<0.05 compared with infected saline treatment group.

Figure 7:
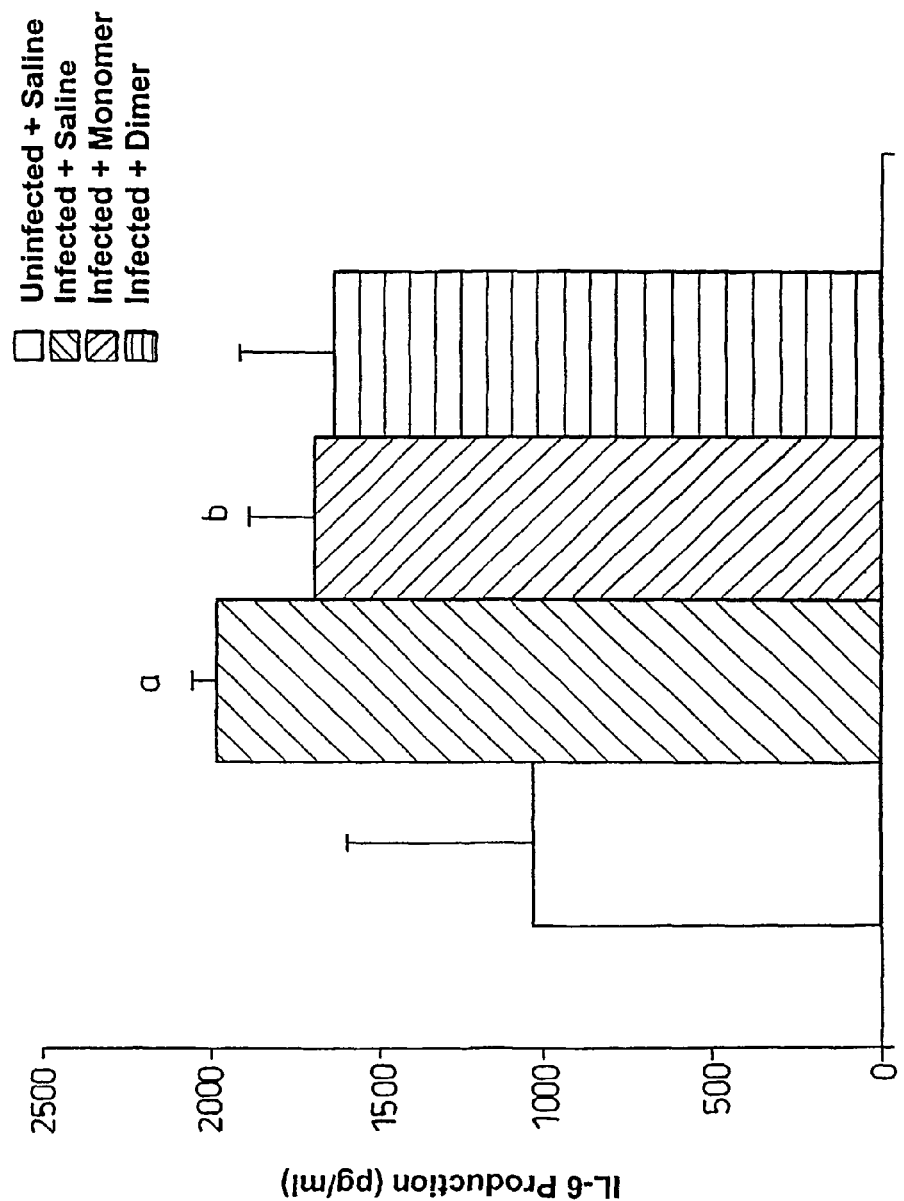

FIG. 7. Interleukin-6 production of splenocyte. LP-BM5 infection significantly (p<0.05) increased IL-6 production. TCR Vβ3 monomer treatments at doses 200 μg/mouse significantly (p<0.05) normalized IL-6 secreted by mitogen-stimulated splenocytes. "a" indicates significant differences at p<0.05 compared with uninfected saline treatment group. "b" indicates significant differences at p<0.05 compared with infected saline treatment group.

EXAMPLE 1

Manufacture of Vβ3 Manomer and Dimer Peptide

The 16-mer Vβ3 peptide may be produced using solid phase peptide synthesis employing 9-Fluorenylmethoxycarbonyl (Fmoc) protecting chemistry.

Solid phase synthesis performed by incorporating the C-terminal end of the amino acid to an amino group in an appropriate support, such as a polymeric styrene resin. The peptide chain is formed by coupling the C-terminal of the next amino acid in the peptide chain to the N-terminal of the amino acid that was previously coupled to the solid support (Fmoc-Thr[tBU]-CTC resin). The completion of each coupling is monitored. If the coupling is incomplete, a new preparation of the amino acid is added to allow a second coupling. When necessary, activation reagents and base are employed.

After completing the synthesis of the total peptide sequence, a final DMF wash of the peptide resin is followed by washing with dichloromethane, and with methanol in preparation for drying. The peptide resin cake is then dried.

Next, the peptide is cleaved from the solid support using TFA, extracted, and dried to yield a powder which is then purified. Crude peptide is purified using preparative reversed phase high performance liquid chromatography followed by a salt exchange chromatographic step. At each step of the purification, fractions meeting the purity specifications are pooled. Following the final acetate-exchange step to produce the Vβ3 peptide as the acetate salt, pooled fractions are lyophilized to give pure 16-mer.

When mixed with sodium-phosphate-mannitol buffer (adjusted pH 5) while maintaining the solution at room temperature for 5 hours, the peptide dimerizes in solution to yield greater than 90% peptide dimer content.

EXAMPLE 2

Animals and Treatment

Female C57BL/6 mice, four weeks old, were obtained from the Charles River Laboratories Inc. (Wilmington, Del.). Animals were cared for as required by the University of Arizona Committee on Animal Research. After two weeks housing in the Central Animal Facility, University of Arizona, they were randomly assigned to one of the following treatment groups: uninfected normal mice (four mice); LP-BM5-infected mice treated with saline (pyrogen free; six mice); LP-BM5-infected mice treated with 200 µg TCR Vβ3 monomer peptide (six mice); LP-BM5-infected mice treated with 200 µg TCR Vβ3 dimer peptide (six mice). LP-BM5 retrovirus was administered intraperitoneally to mice in 0.1 ml saline with an esotropic titre (XC) of 4.5 log 10 plaque-forming units (PFU) per ml. which induces disease with a time course comparable to that previously published. Intraperitoneal administration of monomer and dimer peptides (dissolved in saline) was performed two and six weeks after LP-BM5 infection. Infection to of these mice with LP-BM5 retrovirus leads to the rapid induction of clinical symptoms with virtually no latent phase.

Further Disclosure

Certain uses of the dimer peptide disclosed herein go beyond the uses of the monomer peptide that were disclosed in U.S. Pat. No. 5,911,990. A further aspect of the present invention comprises such further uses of the monomer peptide (or a variant thereof), as disclosed herein for the dimer. Such further uses include: elevating Th1-type activity and or suppressing Th2-type activity; treating cancers (especially in immunocompromised patients); treating infections such as Listeria, Coccidiosis, Leishmaniasis, leprosy and Mycobacteria; treating auto-immune diseases (such as rheumatoid arthritis etc, as disclosed above); treating cardiac complaints (especially those associated with viral infections in HIV-infected and/or immunosuppressed patients); treating immunosenescence; use as an adjuvant in vaccines such as influenza vaccines; and treating allergic diseases such as asthma etc as disclosed above.

The monomer peptide (T-cell receptor Vβ CDR1 peptide) may be made, formulated and administered as disclosed in U.S. Pat. No. 5,911,990, which is incorporated herein by reference.

The following references are specifically incorporated herein by reference. The references cited in the above portion of the description are also incorporated herein by reference.
1. Watson, R. R. 1989, Minireview of murine models for acquired immune deficiency syndrome. Life Sci, 44:iii.
2. Fauci, A. S. 1993, Multifactorial nature of human immunodeficiency virus disease: implications for therapy, Science 262:1011.
3. Selvey, L. A., H. C. Mose III, L. G. Graner, and R. J. Hodes, 1993. Preferential expansion and activation of Vβ5+ CD4+ T cells in murine acquired immunodeficiency syndrome. J. Immunol. 151:1712.
4. Soudeyns, H. N. Rebai, G. P. Pantaleo, C. Ghali, T. Boghossian, P. P. Sekaly, and A. S. Fauci, 1993. The T cell receptor Vβ repertoire in HIV-1 infection and disease, Semin. Immunol. 5:175.
5. Imberti, L., A. Sottini, A. Bettinaridi, M. Puoti, and D. Primi, 1991. Selective depletion in HIV infection of T cells that bear specific T cell receptor Vβ sequences. Science 254:860.
6. Clerici, M., and G. M. Shearer, 1993. A Th1-->Th 2 switch is a critical step in the etiology of HIV infection. Immunol. Today 14:107.
7. Bradley, W. G., N. Ogata, R. A. Good, and N. K. Day, 1993. Alteration of in vivo cytokine gene expression in mice infected with a molecular clone the defective MAIDS virus. J. AIDS 7:1.
8. Sher, A., R. T. Gazzinelli, I. P. Oswald, M. Clerici, M. Kullberg, E. J. Pearce, J. A. Berzofsky, T. R. Mosmann, S. L. James, H. C. Morse III, and G. M. Shearer, 1992. Role of T-cell derived cytokines in the downregulation of immune responses in parasitic and retroviral infection. Immunol. Rev. 127:183.
9. Wang, Y., D. S. Huang, P. T. Giger, and R. R. Watson, 1993. The kinetics of imbalanced cytokine production by T cells and macrophages during the murine AIDS, Adv. Biosci. 86:335.
10. Gazzinelli, R. T., M. Makino, S. K. Chattopadhyay, C. M. Sanpper, A. Sher, A. W. Hugin, and H. C. Morse III, 1992. Preferential activation of Th2 cells during progression of retrovirus-induced immunodeficiency in mice. J. Immunol. 148:182.
11. Kanagawa, O., B. A. Vaupel, S. Gayama, G. Koehler, and M. Kopf, 1993. Resistance of mice deficient in IL-4 to retrovirus-induced immunodeficiency syndrome (MAIDS). Science 262:240.
12. Wang, Y., S. K. Ardestain, B. Liang, L. Beckham, and R. R. Watson, 1994. Anti-IL-4 monoclonal antibody and interferon-γ administration retards development of immune dysfunction and cytokine dysregulation during murine AIDS. Immunology 83:384.
13. Marchalonis, J. J., K. Deghanpisheh, D. Huang, S. F. Schluter, and R. R. Watson, 1994. Autoantibodies to T-cell receptors following infection by murine retrovirus. Lymphology 27S:853.
14. Victor-Korbin, C., F. A. Bonilla, Z. Barak, and C. Bona, 1989. Structural correlates of a regulatory idiotype. Immunol. Rev. 1110:151.

The invention claimed is:

1. A dimer comprising a monomer that
  (a) consists of, from the N-terminus to the C-terminus direction, the sequence Cys Lys Pro Ile Ser Gly His Asn Ser Leu Phe Trp Tyr Arg Gln Thr (SEQ ID NO:1) with the proviso that, if the sequences are present as an aqueous solution, then at least 81% of the occurrences of the sequence are present as a dimer; or
  (b) is a homolog of the β3 peptide of the T-cell receptor β chain clone YT35, the said β3 peptide consisting of, from the N-terminus to the C-terminus direction, the sequence Cys Lys Pro Ile Ser Gly His Asn Ser Leu Phe Trp Tyr Arg Gln Thr (SEQ ID NO:1), wherein the homolog has the sequence of a segment of another distinct human Vβ gene which segment corresponds to the same segment as the said β3 peptide and wherein the homolog has the sequence Cys-[X]-Trp-[Y], wherein

[X] is a 10 or 11 amino acid sequence and wherein [Y] is a 4 amino acid sequence; or (c) is a variant of the monomer of (a) or (b), wherein:

(i) the variant has the sequence Cys-[X]-Trp-[Y], wherein [X] is a 10 or 11 amino acid sequence that has the sequence of amino acids 2-11 of the β3 peptide of the T-cell receptor β chain clone YT35, which is Lys Pro Ile Ser Gly His Asn Ser Leu Phe, or the sequence of the same segment of another distinct human Vβ gene which segment corresponds to the same segment as the said β3 peptide; and (ii) wherein [Y] is a 4 amino acid sequence that has the sequence of amino acids 13-16 of the β3 peptide of the T-cell receptor β chain clone YT35, which is Tyr Arg Gln Thr, or the sequence of the same segment of another distinct human Vβ gene which segment corresponds to the same segment as the said β3 peptide, except that, at one position in total within the [X] and [Y] sequences, there is a substitution wherein the dimer when administered as a dose of 200 μg/mouse to a C57BL/6 mouse infected with the LP-BM5 retrovirus, has the ability to normalize IL-4 secretion by mitogen-stimulated splenocytes of said mouse relative to a C57BL/6 mouse infected with the LP-BM5 retrovirus and treated with saline.

2. The dimer of claim 1 that is a homodimer.

3. A homodimer according to claim 2, wherein each monomer of the homodimer consists of, from the N-terminus to the C-terminus direction, the sequence Cys Ser Pro Lys Ser Gly His Asp Thr Val Ser Trp Tyr Gln Gln Ala (SEQ ID NO:2).

4. A dimer according to claim 1 with the proviso that, if the sequences are present as an aqueous solution, then at least 81% of the occurrences of the sequences are present as a dimer.

5. A pharmaceutical formulation comprising a dimer according to claim 1 and a pharmaceutically acceptable excipient.

6. A method for treating an infectious disease caused by an immunodeficiency-type retrovirus, the method comprising administering a composition comprising a dimer of claim 1 to an animal in need of treatment.

7. The method of claim 6 wherein the immunodeficiency-type retrovirus is a C-type retrovirus or a lentivirus.

8. The method of claim 7 wherein the lentivirus is HIV-1, HIV-2, HIV-3, simian immunodeficiency virus (SIV), or feline immunodeficiency virus (FIV).

9. A pharmaceutical formulation comprising a dimer of claim 1 wherein at least 82%, 83%, 84%, 85%, 88%, 90%, 92%, 95%, 98%, 99%, 99.5%, 99.9%, 99.99%, 99.999% or substantially 100% of the occurrences of the sequences are present as a dimer.

10. A composition comprising a dimer of claim 1 and a further therapeutic agent.

11. The composition of claim 10 wherein the further therapeutic agent is a peptide or an immune-stimulating adjuvant.

12. The composition of claim 10 wherein the further therapeutic agent is useful in the treatment of HIV-infection.

13. The composition of claim 10 wherein the further therapeutic agent is an antibiotic or an anti-histamine.

* * * * *

UNITED STATES PATENT AND TRADEMARK OFFICE
CERTIFICATE OF CORRECTION

PATENT NO. : 7,998,926 B2
APPLICATION NO. : 10/478194
DATED : August 16, 2011
INVENTOR(S) : John J. Marchalonis et al.

Page 1 of 1

It is certified that error appears in the above-identified patent and that said Letters Patent is hereby corrected as shown below:

On the cover page (bibliographic data):

At section (73), under "Assignee" data, please replace

"The Arizona Boad of Regents on Behfl of the University of Arizona, Tucson, AZ (US)"

with

--The Arizona Board of Regents on Behalf of the University of Arizona, Tucson, AZ (US)--.

Signed and Sealed this
Eighteenth Day of October, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Beta-3 peptide of T cell receptor Beta chain clone YT35

<400> SEQUENCE: 1

Cys Lys Pro Ile Ser Gly His Asn Ser Leu Phe Trp Tyr Arg Gln Thr
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Beta-5.2 peptide of T cell receptor Beta chain

<400> SEQUENCE: 2

Cys Ser Pro Lys Ser Gly His Asp Thr Val Ser Trp Tyr Gln Gln Ala
1               5                   10                  15

<210> SEQ ID NO 3
<211> LENGTH: 32
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Homodimer containing Beta-3 peptide

<400> SEQUENCE: 3

Thr Gln Arg Tyr Trp Phe Leu Ser Asn His Gly Ser Ile Pro Lys Cys
1               5                   10                  15

Cys Lys Pro Ile Ser Gly His Asn Ser Leu Phe Trp Tyr Arg Gln Thr
                20                  25                  30

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Presumed T cell epitope

<400> SEQUENCE: 4

Thr Ala Ser Gly Val Ala Glu Thr Thr Asn Cys
1               5                   10